(12) United States Patent
Bruna et al.

(10) Patent No.: US 7,389,946 B2
(45) Date of Patent: Jun. 24, 2008

(54) FLUID PRODUCT SPRAYING DEVICE

(75) Inventors: Pascal Bruna, Sotteville les Rouen (FR); Matthieu Savalle, Rouen (FR)

(73) Assignee: Valois S.A.S, Le Neubourg (FR)

( * ) Notice: Subject to any disclaimer, the term of this patent is extended or adjusted under 35 U.S.C. 154(b) by 127 days.

(21) Appl. No.: 10/528,557

(22) PCT Filed: Sep. 19, 2003

(86) PCT No.: PCT/FR03/02765

§ 371 (c)(1), (2), (4) Date: Mar. 21, 2005

(87) PCT Pub. No.: WO2004/026379

PCT Pub. Date: Apr. 1, 2004

(65) Prior Publication Data

US 2005/0258273 A1    Nov. 24, 2005

(30) Foreign Application Priority Data

Sep. 20, 2002    (FR) .................................. 02 11791

(51) Int. Cl.
   *B05B 9/04*    (2006.01)

(52) U.S. Cl. ......................... 239/320; 239/74; 239/309; 239/600; 222/82; 222/83; 222/327; 222/386; 222/505

(58) Field of Classification Search ................ 239/302, 239/315, 331, 600, 337, 338, 271, 272, 309, 239/140, 373, 71, 74, 320, 321; 604/415, 604/232; 222/82, 83, 325–327, 386, 391, 222/505, 507, 509; 220/581, 583
See application file for complete search history.

(56) References Cited

U.S. PATENT DOCUMENTS

| | | | | |
|---|---|---|---|---|
| 608,349 A | * | 8/1898 | Sterne | 220/581 |
| 1,495,924 A | | 5/1924 | Quale | |
| 1,920,165 A | * | 8/1933 | Andvig | 239/309 |
| 2,098,454 A | * | 11/1937 | Kelley, Jr. | 222/509 |

(Continued)

FOREIGN PATENT DOCUMENTS

FR    1242253 A    9/1960

OTHER PUBLICATIONS

International Search Report for PCT/FR03/02765 dated Feb. 19, 2004.

*Primary Examiner*—Steven J Ganey
(74) *Attorney, Agent, or Firm*—Sughrue Mion, PLLC

(57) ABSTRACT

A fluid spray device having a body (10) provided with a spray orifice (15), a reservoir (20) containing the fluid to be sprayed, a spray device (30) that sprays one or more doses of the fluid contained in the reservoir (20); and an actuator (40) that actuates the spray device (30). The reservoir (20) is closed in a sealed manner before the spray device is actuated for the first time, the body (10) including reservoir opening device (11) adapted to open the reservoir (20) while the device is being actuated. The reservoir (20) forms a sealed unit that is separate from the body (10), filled with fluid and hermetically sealed before it is assembled in the body (10). The body (10) includes a receiver device (13) that receives the reservoir, and a lateral access device that enables the filled reservoir (20) to be assembled sideways into the body (10) and to be secured therein.

19 Claims, 1 Drawing Sheet

U.S. PATENT DOCUMENTS

| | | | |
|---|---|---|---|
| 2,316,095 A | 4/1943 | Mead, Jr. | |
| 2,362,784 A * | 11/1944 | Ward | 239/309 |
| 2,666,667 A * | 1/1954 | Ward | 222/82 |
| 2,895,633 A * | 7/1959 | Zellweger | 220/583 |
| 3,905,365 A * | 9/1975 | Colombo | 604/209 |
| 4,444,560 A * | 4/1984 | Jacklich | 604/224 |
| 4,446,990 A * | 5/1984 | Stevenson et al. | 222/82 |
| 4,581,022 A * | 4/1986 | Leonard et al. | 604/229 |
| 4,860,738 A * | 8/1989 | Hegemann et al. | 128/200.22 |
| 5,137,528 A * | 8/1992 | Crose | 604/415 |
| 5,307,953 A * | 5/1994 | Regan | 222/82 |
| 5,433,352 A * | 7/1995 | Ronvig | 222/391 |
| 5,480,390 A * | 1/1996 | Hajishoreh | 604/192 |
| 5,542,934 A * | 8/1996 | Silver | 604/191 |
| 6,145,703 A * | 11/2000 | Opperman | 222/82 |
| 6,382,465 B1 * | 5/2002 | Greiner-Perth | 222/82 |
| 6,708,846 B1 * | 3/2004 | Fuchs et al. | 222/82 |
| 6,745,760 B2 * | 6/2004 | Grychowski et al. | 128/200.14 |
| 2002/0023641 A1 | 2/2002 | Stadelhofer | |

* cited by examiner

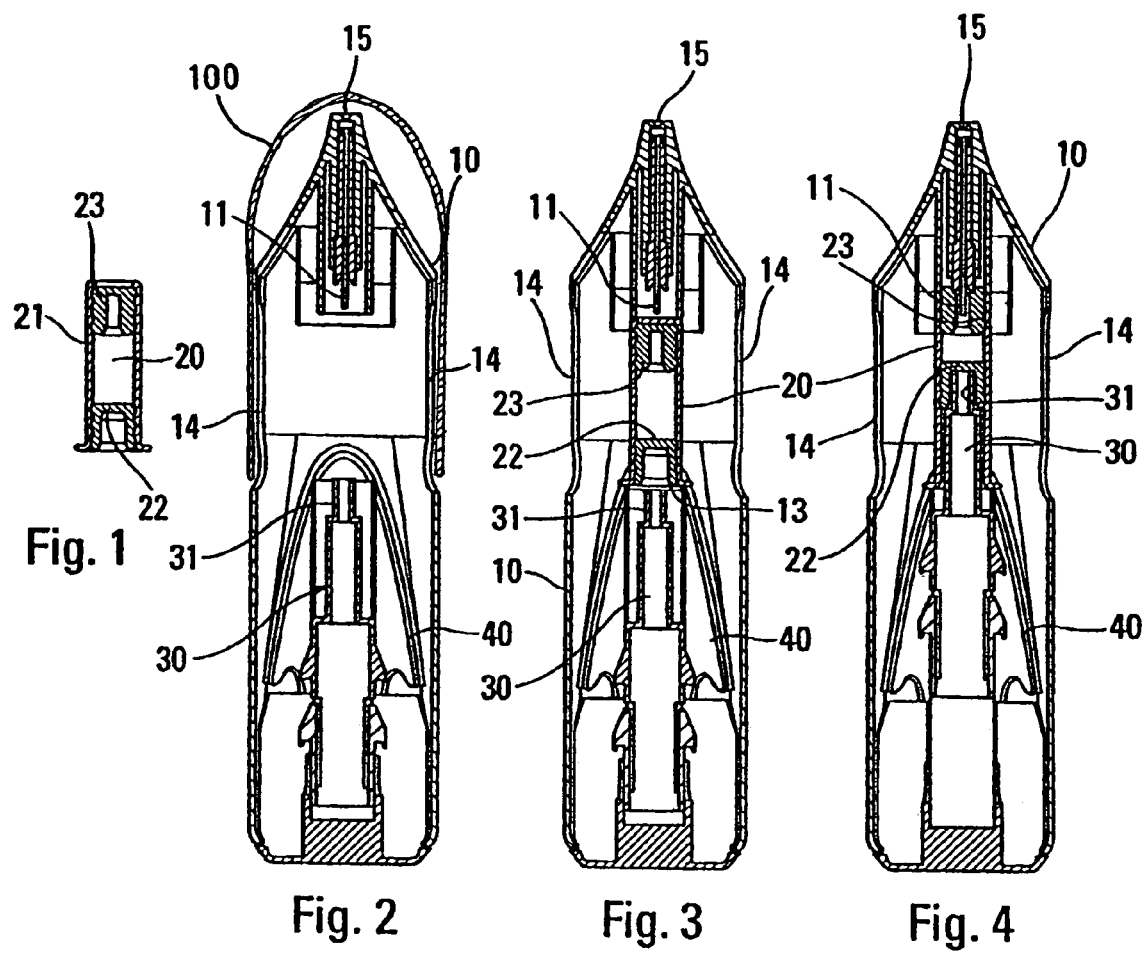
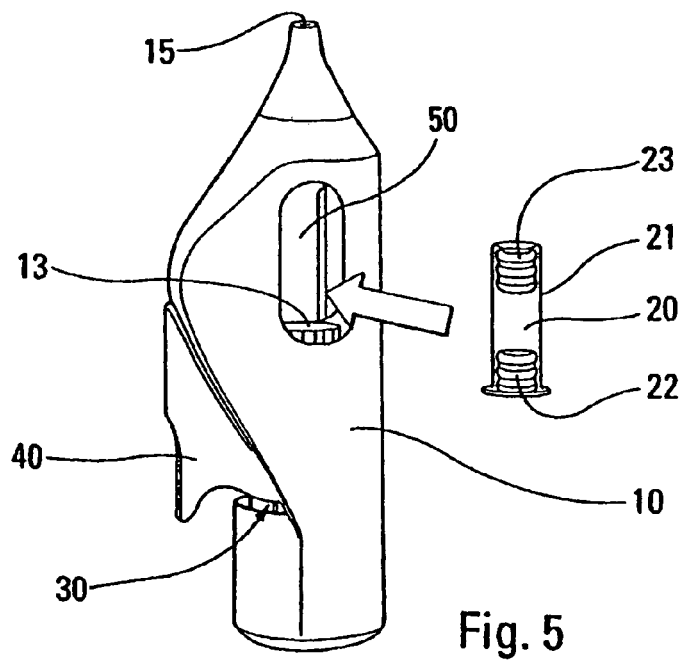

FLUID PRODUCT SPRAYING DEVICE

FIELD OF THE INVENTION

The present invention relates to a fluid spray device, and more particularly to a nasal spray device of the two-dose type, i.e. containing two doses of fluid to be dispensed.

BACKGROUND ART

Spray devices of the two-dose type have been developed for numerous applications, in particular in the field of pharmacy. In particular, such devices are used in the field of nasal sprays. Such a device generally has a reservoir containing two doses of fluid, each dose being intended for a respective nostril.

Depending on the nature of the fluid, particularly when it is medicine, the filling and storage conditions for the fluid can be quite restricting. Thus, in the pharmaceutical field, numerous fluids, i.e. liquids or powders, need to be filled in a sterile zone, and need to be stored in a cold room. Existing spray devices are generally filled with fluid after the device has been fully assembled, thereby implying filling machines that are specially adapted to the devices in question, which machines must naturally be in sterile zones. After filling, the device as a whole must be stored in a cold room. Given the very high costs of surface area in sterile zones and of cubic capacity in cold rooms, the use of specific filling machines turns out to be a drawback in terms of cost, and the same applies to storage in a cold room, since the volume of a nasal spray device is often rather large.

BRIEF SUMMARY OF THE INVENTION

An object of the present invention is to provide a fluid spray device which does not have the above-mentioned drawbacks.

Thus, an object of the present invention is to provide a fluid spray device for which the requirements in sterile-zone surface area during filling, and in cold-room cubic capacity during storage are as small as possible.

Another object of the present invention is to provide such a fluid spray device which is simple and inexpensive to manufacture and to assemble, and which operates in reliable manner.

The present invention thus provides a fluid spray device comprising: a body provided with a spray orifice, a reservoir containing the fluid to be sprayed, spray means for spraying one or more doses of the fluid contained in the reservoir; and actuator means for actuating said spray means, said reservoir being closed in sealed manner before the spray device is actuated for the first time, the body including reservoir opening means adapted to open said reservoir while the device is being actuated, said device being characterized in that said reservoir forms a sealed unit that is separate from said body, said reservoir being filled with fluid and being sealed hermetically before it is assembled in said body, and in that said body includes receiver means for receiving the reservoir, and lateral access means for enabling said filled reservoir to be assembled sideways into said body and to be secured therein.

Advantageously, said lateral access means comprise a window provided in a side wall of said body.

Advantageously, said lateral access means comprise two diametrally-opposite windows.

Advantageously, said receiver means for receiving the reservoir comprise snap-fastener means for snap-fastening the reservoir in said body.

Advantageously, said reservoir is formed by a hollow tube that is closed in sealed manner by first and second plugs disposed in said tube, the fluid being disposed between said first and second plugs.

Advantageously, the spray means include an axially-displaceable rod that co-operates with the first plug of said reservoir.

Advantageously, said actuator means include a lateral actuator element that is displaceable in a direction that is different from the displacement direction of said spray means.

Advantageously, said reservoir opening means include piercing means for piercing the second plug of the reservoir.

Advantageously, the spray means, the actuator means, and the reservoir opening means are assembled to form a unit, the reservoir being assembled in said unit after said reservoir has been filled and plugged.

Advantageously, said lateral access means include a removable cover.

Advantageously, the reservoir contains two doses of fluid, said spray means and/or said actuator means including dose-fractioning means, so that each time the device is actuated, one dose of fluid is sprayed.

BRIEF DESCRIPTION OF THE SEVERAL VIEWS OF THE DRAWING(S)

Other characteristics and advantages of the present invention appear more clearly from the following detailed description, given by way of non-limiting example, and with reference to the accompanying drawing, and in which:

FIG. 1 is a diagrammatic section view of a fluid reservoir for a fluid spray device constituting an advantageous embodiment of the present invention;

FIG. 2 is a diagrammatic section view of a fluid spray device constituting an advantageous embodiment of the present invention, into which the FIG. 1 reservoir can be fitted;

FIG. 3 is a view similar to the view in FIG. 2, showing the reservoir secured inside the device;

FIG. 4 is a view similar to the view in FIG. 3, after the device has been actuated; and FIG. 5 is a diagrammatic perspective view of a fluid spray device constituting an advantageous embodiment of the present invention, showing the device and the reservoir separately.

DETAILED DESCRIPTION OF THE INVENTION

FIG. 1 shows a reservoir 20 that is adapted to the fluid spray device of the present invention. The reservoir forms a sealed unit that is separate from the remainder of the device, and that is advantageously constituted by a hollow tube 21 which is plugged at each end by respective first and second sealing plugs 22, 23. This type of reservoir can be made of glass, or of any other suitable material, and the plugs 22, 23 can be made of elastomer material, or of any other material that is suitable for sealing its content inside the reservoir 20 after it has been filled. This type of reservoir is therefore very small in size, in particular when it contains only two doses of fluid, thereby limiting the sterile-zone surface area needed for filling the reservoirs, and the cold-room cubic capacity needed for storing said reservoirs after they have been filled.

FIG. 2 is a diagrammatic view of a spray device into which the FIG. 1 reservoir can be fitted. The device comprises a body 10 which is provided with a spray orifice 15. The body 10 comprises opening means 11 for opening the reservoir 20, which means could be formed by piercing means for example, such as a needle. The needle 11 is preferably stationary relative to the body 10 and is disposed facing, or connected to, the spray orifice 15, the needle being designed to pierce the second plug 23 of the reservoir 20 while the device is being actuated. The spray device further comprises spray means 30, and actuator means 40 for actuating said spray means. Spraying is an important aspect, in particular for nasal spray devices, which must spray the fluid finely so as to provide optimum therapeutic effectiveness. The spray means 30 advantageously include a rod, or an element that is similar to a rod, that is axially displaceable, and that is adapted to co-operate with the first plug 22 of the reservoir 20 so as to displace said plug axially as a piston inside the reservoir 20. In known manner, the displacement of the first plug 22 inside the reservoir raises the pressure inside said reservoir, and therefore causes the second plug 23 to be displaced towards the needle 11, until said needle pierces the plug 23 and puts the contents of the reservoir 20 into communication with the spray orifice 15. The actuator means 40 preferably comprise a lateral actuator element, i.e. an element which is displaced in a direction that is different from the direction of displacement of the spray means 30. By way of example, the lateral actuator element 40 can be made as a pivot tab which is mounted on the body 10, and which co-operates with the spray means 30 so as to displace said spray means during actuation. Naturally, different spray and actuator means could be envisaged. In the case of a two-dose device, dose-fractioning means are advantageously provided to split the contents of the reservoir into two doses. The dose-fractioning means can be provided on the spray means 30 and/or on the actuator means 40. The dose-fractioning means are not described in greater detail below since they are not connected directly to the present invention, and since they can be of any form.

In the invention, the body 10 includes receiver means 13 for receiving the reservoir, and lateral access means 50. The lateral access means 50 enable the reservoir 20 to be loaded sideways into the body 10, so that the reservoir can be assembled inside the body just before the device is used. The reservoir is thus assembled inside a complete unit formed by the body, the spray means, the actuator means, and the reservoir opening means. The lateral access means advantageously include at least one window 14 made in a side wall of the body 10. The figures show a body 10 including two diametrally-opposite lateral windows 14. The receiver means 13 for receiving the reservoir can be made in the form of snap-fastener means, or of any other suitable means that enable the reservoir 20 to be received securely inside the body 10. Naturally, complementary fastener or abutment means (not shown) can be provided to enable the reservoir to be secured better in the body. A removable cover (100) could possibly be provided for the lateral window(s) 14, which cover can be made in any desirable way.

Loading the reservoir sideways into the body therefore enables a reservoir to be made separately, to be filled, to be plugged hermetically, and then to be stored independently from the remainder of the spray device. The remainder of the spray device can itself be assembled in a non-sterile zone and stored in a location other than a cold room. The reservoir can be assembled inside the body 10 just before the device is used, the contents of the reservoir remaining protected by the sealed plugs 22, 23 until the device is actuated for the first time. Loading the reservoir sideways presents the advantage of making it possible to use lateral actuation with spray means being displaced in axial manner, and to assemble the device as a whole, without the reservoir. Assembly of the device is simplified, and the device itself is also simplified, making a saving in particular of a part that is generally required for pre-assembling the reservoir, when said reservoir is to be assembled axially inside the body. The present invention therefore enables a fluid spray device to be made that is less costly, that operates in reliable manner, and for which considerable savings can be made during filling and storage.

Although the invention is described above with reference to a particular embodiment thereof, any modifications could naturally be applied thereto by a person skilled in the art, without going beyond the ambit of the present invention as defined by the accompanying claims.

The invention claimed is:

1. A fluid spray device comprising: a body (10) provided with a spray orifice (15), a reservoir (20) containing the fluid to be sprayed, spray means (30) for spraying one or more doses of the fluid contained in the reservoir (20); and actuator means (40) for actuating said spray means (30), said reservoir (20) being closed in sealed manner before the spray device is actuated for the first time, the body (10) including reservoir opening means (11) adapted to open said reservoir (20) while the device is being actuated, said reservoir (20) forming a sealed unit that is separate from said body (10), said reservoir (20) being filled with fluid and being sealed hermetically before it is assembled in said body (10), and said body (10) including receiver means (13) for receiving the reservoir, and lateral access means (50) for enabling said filled reservoir (20) to be assembled sideways into said body (10) and to be secured therein, said device being characterized in that said actuator means (40) include a lateral actuator element that is displaceable in a direction that is different from the displacement direction of said spray means (30);

wherein the lateral actuator element is displaceable in a direction transverse to the displacement direction of the spray means; and wherein the reservoir opening means comprises a needle.

2. A device according to claim 1, in which said lateral access means comprise a window (14) provided in a side wall of said body (10).

3. A device according to claim 2, in which said lateral access means comprise two diametrically-opposite windows (14).

4. A device according to claim 1, in which said receiver means (13) for receiving the reservoir comprise snap-fastener means for snap-fastening the reservoir (20) in said body (10).

5. A device according to claim 1, in which said reservoir (20) is formed by a hollow tube (21) that is closed in sealed manner by first and second plugs (22, 23) disposed in said tube (21), the fluid being disposed between said first and second plugs (22, 23).

6. A device according to claim 5, in which the spray means (30) include an axially-displaceable rod (31) that co-operates with the first plug (22) of said reservoir (20) to displace the first plug.

7. A device according to claim 5, in which said reservoir opening means (11) include piercing means for piercing the second plug (23) of the reservoir (20).

8. A device according to claim 1, in which the body (10), the spray means (30), the actuator means (40), and the reservoir opening means (11) are assembled to form a unit, the reservoir (20) being assembled in said unit after said reservoir has been filled and plugged.

9. A device according to claim 1, in which said lateral access means (50) include a removable cover.

10. The device according to claim 1, wherein the lateral actuator element is a pivot tab that is displaced towards a longitudinal axis of the body.

11. A fluid spray device comprising:
a body comprising a spray orifice;
a reservoir comprising a fluid to be sprayed;
a spray mechanism that sprays at least one of the fluid; and
an actuator element that actuates the spray mechanism; and wherein:
the reservoir is separate from the body, filled with fluid, sealed prior to assembly in the body and remains sealed until the spray mechanism is actuated for a first time;
the body comprises an opening device that opens the reservoir as the fluid spray device is actuated;
the body comprises a support for the reservoir and at least one side opening through which the reservoir is inserted into the body and secured on the support; and
the actuator element is displaceable in a direction transverse to an axial displacement direction of said spray mechanism; and
wherein the opening device is a needle.

12. The device according to claim 11 that is structured to be a nasal spray device configured for dispensing a dose of fluid into the nasal cavity.

13. The device according to claim 12, wherein the fluid is formulated for application through the nasal cavity.

14. The device according to claim 11, wherein the spray mechanism is a rod moveable in a longitudinal axial direction of the body and the reservoir.

15. The device according to claim 11, wherein the support snap-fastens with the reservoir.

16. The device according to claim 11, wherein actuator element is a pivot tab.

17. The device according to claim 11, wherein the actuator element is a pivot tab that is displaced towards a longitudinal axis of the body.

18. A fluid spray device comprising: a body provided with a spray orifice, a reservoir containing the fluid to be sprayed, spray means for spraying one or more doses of the fluid contained in the reservoir; and actuator means for actuating said spray means, said reservoir being closed in sealed manner before the spray device is actuated for the first time, the body including reservoir opening means adapted to open said reservoir while the device is being actuated, said reservoir forming a sealed unit that is separate from said body, said reservoir being filled with fluid and being sealed hermetically before it is assembled in said body, and said body including receiver means for receiving the reservoir, and lateral access means for enabling said filled reservoir to be assembled sideways into said body and to be secured therein, said device being characterized in that said actuator means include a lateral actuator element that is displaceable in a direction that is different from the displacement direction of said spray means;
wherein the lateral actuator element is displaceable in a direction transverse to the displacement direction of the spray means;
wherein said reservoir is formed by a hollow tube that is closed in sealed manner by first and second plugs disposed in said tube, the fluid being disposed between said first and second plugs; and
wherein the spray means includes an axially-displaceable rod that co-operates with the first plug of said reservoir to displace the first plug.

19. A fluid spray device comprising: a body provided with a spray orifice, a reservoir containing the fluid to be sprayed, spray means for spraying one or more doses of the fluid contained in the reservoir; and actuator means for actuating said spray means, said reservoir being closed in sealed manner before the spray device is actuated for the first time, the body including reservoir opening means adapted to open said reservoir while the device is being actuated, said reservoir forming a sealed unit that is separate from said body, said reservoir being filled with fluid and being sealed hermetically before it is assembled in said body, and said body including receiver means for receiving the reservoir, and lateral access means for enabling said filled reservoir to be assembled sideways into said body and to be secured therein, said device being characterized in that said actuator means include a lateral actuator element that is displaceable in a direction that is different from the displacement direction of said spray means;
wherein the lateral actuator element is displaceable in a direction transverse to the displacement direction of the spray means;
wherein said reservoir is formed by a hollow tube that is closed in sealed manner by first and second plugs disposed in said tube, the fluid being disposed between said first and second plugs; and
wherein said reservoir opening means includes piercing means for piercing the second plug of the reservoir.

* * * * *